US00PP12852P2

(12) United States Plant Patent
Jacobsen

(10) Patent No.: US PP12,852 P2
(45) Date of Patent: Aug. 13, 2002

(54) POINSETTIA PLANT NAMED 'JACAIMEE'

(75) Inventor: Aase Jacobsen, Skibby (DK)

(73) Assignee: Paul Ecke Ranch, Encinitas, CA (US)

( * ) Notice: Subject to any disclaimer, the term of this patent is extended or adjusted under 35 U.S.C. 154(b) by 55 days.

(21) Appl. No.: 09/779,348

(22) Filed: Feb. 9, 2001

(51) Int. Cl.[7] ..... A01H 5/00
(52) U.S. Cl. ..... Plt./304
(58) Field of Search ..... Plt./304

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of Poinsettia plant named 'Jacaimee', characterized by its inflorescences with creamy white-colored flower bracts; dark green-colored leaves with green-colored petioles; compact, uniform and upright plant habit; freely branching habit; early flowering, natural season flower maturity date is November 15 for plants grown in Encinitas, Calif.; response time, about 7.5 weeks; and excellent post-production longevity.

2 Drawing Sheets

BACKGROUND OF THE INVENTION

The present Invention relates to a new and distinct cultivar of Poinsettia plant, botanically known as *Euphorbia pulcherrima* Willd., and hereinafter referred to by the name 'Jacaimee'.

The new Poinsettia a product of a planned breeding program conducted by the Inventor in Skibby, Denmark. The objective of the breeding program is to create new Poinsettia cultivars having flower bracts with desirable colors, uniform plant habit and excellent post-production longevity.

The new Poinsettia is an induced mutation of the Poinsettia cultivar Pepride, disclosed in U.S. Plant Pat. No. 10,183. Plants of the new Poinsettia originated by exposing unrooted cuttings of the Poinsettia cultivar Pepride to X-ray radiation. The new Poinsettia was discovered and selected by the Inventor as a single flowering plant within a population of irradiated plants in a controlled environment in Skibby, Denmark, in 1998. The selection of this plant was based on its attractive flower bract colors and good plant form and substance.

Asexual reproduction of the new Poinsettia by terminal cuttings taken at Encinitas, Calif., since 1999, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Jacaimee'. These characteristics in combination distinguish 'Jacaimee' as a new and distinct cultivar:

1. Inflorescences with creamy white-colored flower bracts.
2. Dark green-colored leaves with green-colored petioles.
3. Compact, uniform and upright plant habit.
4. Freely branching habit.
5. Early flowering, natural season flower maturity date is November 15 for plants grown in Encinitas, Calif.; response time, about 7.5 weeks.
6. Excellent post-production longevity.

Plants of the new Poinsettia can be compared to plants of the mutation parent, the cultivar Pepride. In side-by-side comparisons conducted in Encinitas, Calif., plants of the new Poinsettia differed from plants of the cultivar Pepride in the following characteristics:

1. Plants of the new Poinsettia are more compact and not as vigorous as plants of the cultivar Pepride.
2. Flower bract color of plants of the new Poinsettia is cream white whereas flower bract color of plants of the cultivar Pepride is red.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph on the first sheet comprises a side perspective view of a typical plant of 'Jacaimee'.

The photograph at the top of the second sheet comprises a top perspective view of a typical plant of 'Jacaimee'.

The photograph at the bottom of the second sheet is a close-up view of typical leaves and flower bracts of 'Jacaimee' (top) and 'Pepride' (bottom). Plants used in the photographs were about 16 weeks old; cyathia on the plants of the new Poinsettia were not completely developed when the photographs were taken.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures about 24° C., night temperatures about 19° C., and light levels about 4,000 foot-candles. Single plants were grown in 16.5-cm pots, pinched one time, and flowered under naturally lengthening nyctoperiods during the fall. Plants used for the description were about 16 to 18 weeks old.

In the following description, color references are made to The Royal Horticultural Society Colour Chart except where general terms of ordinary dictionary significance are used.

Botanical classification: *Euphorbia pulcherrima* Willd. cultivar Jacaimee.

Parentage: Induced mutation of *Euphorbia pulcherrima* Willd. cultivar Pepride, disclosed in U.S. Plant Pat. No. 10,183.

Propagation:

*Type cutting.*—Terminal cuttings.

*Time to initiate roots.*—About 10 days at 20 to 22° C.

*Time to develop roots.*—About 28 days at 20 to 22° C.

*Rooting habit.*—Thick, fibrous and freely-branching.

Plant description:

*Plant form.*—Inverted triangle, top of plant rounded; mounding.

*Growth habit.*—Uniform, compact and upright plant habit. Upright branch angle. Freely branching; branching is enhanced by removing the shoot apex; about 5 lateral branches develop after removal of the terminal apex. Moderate vigor.

*Plant height.*—About 22 cm.

*Plant diameter or spread.*—About 45 cm.

*Crop time.*—From unrooted cuttings to a flowering plant in a 16.5-cm container, about 16 weeks are required.

*Stem description.*—Lateral branch length: About 19 cm. Lateral branch diameter: About 1.2 cm. Internode length: About 1.5 cm. Stem color: 137C.

*Foliage description.*—Alternate, simple. Quantity of leaves per lateral branch: About 9. Length: About 9 cm. Width: About 6 cm. Shape: Mostly ovate; irregularly lobed. Apex: Acuminate. Base: Acute to rounded. Margin: Entire. Texture: Mostly glabrous with very slight pubescence on lower surface. Surface: Smooth, not rugose. Color: Young foliage, upper surface: Darker than 147A. Young foliage, lower surface: 147B. Mature foliage, upper surface: Darker than 147A; venation, 145A. Mature foliage, lower surface: 147A; venation, 145C. Petiole: Length: About 3.5 cm. Diameter: About 2 mm. Color: 145C.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions. Early flowering, response time, about 7.5 weeks; natural season flower maturity date is November 15 for plants grown in Encinitas, Calif.

*Post-production longevity.*—Plants of the new Poinsettia maintain good substance and bract color for about 4 to 6 weeks under interior conditions and for about 8 weeks under greenhouse conditions.

*Quantity of inflorescences.*—One per lateral branch, usually about 5 per plant.

*Inflorescence size.*—Diameter: About 22 cm. Height (depth): About 2.5 cm.

*Flower bracts.*— Quantity of flower bracts per inflorescence: Usually about 12 primary bracts and about 6 to 8 smaller secondary bracts per inflorescence. Length, largest bracts: About 10.5 cm; stalk about 3 cm. Width, largest bracts: About 8 cm. Shape: Mostly ovate, lobed. Apex: Acuminate. Base: Acute. Margin: Entire. Texture: Glabrous, velvety. Surface: Smooth, not rugose. Orientation: Mostly horizontal. Color: Developing, upper surface: More cream than 145A. Developing, lower surface: 144B to 144C. Mature, upper surface: 11C to 12D. Mature, lower surface: Slightly more green than 11C.

*Cyathia.*—Quantity: Usually about 18 per corymb. Diameter of cyathia cluster: About 3 by 3.5 cm. Length: About 7 mm. Width: About 5 mm. Shape: Ovate. Color: Immature: 144A. Mature: 144B to 144C. Peduncle: Length: About 4 mm. Aspect: Strong, erect. Color: 144B. Stamens: Stamen number: Typically about 20 per cyathium. Anther shape: Oval. Anther length: About 1 mm. Anther color: 46A. Amount of pollen: Scarce. Pollen color: 7A. Pistils: Not observed. Nectary number: One per cyathia. Nectary color: 12B.

Disease resistance: Resistance to pathogens common to Poinsettias has not been observed on plants grown under commercial conditions.

It is claimed:

1. A new and distinct cultivar of Poinsettia plant named 'Jacaimee', as illustrated and described.

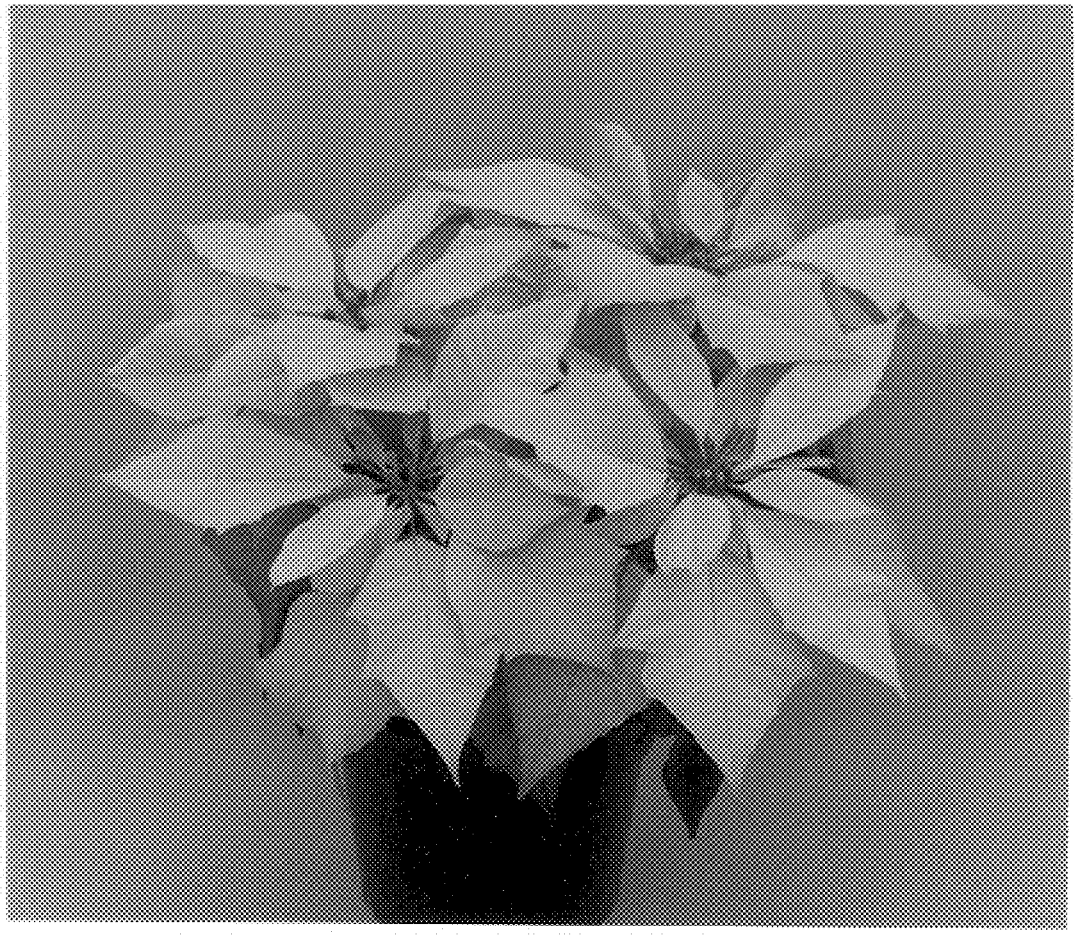

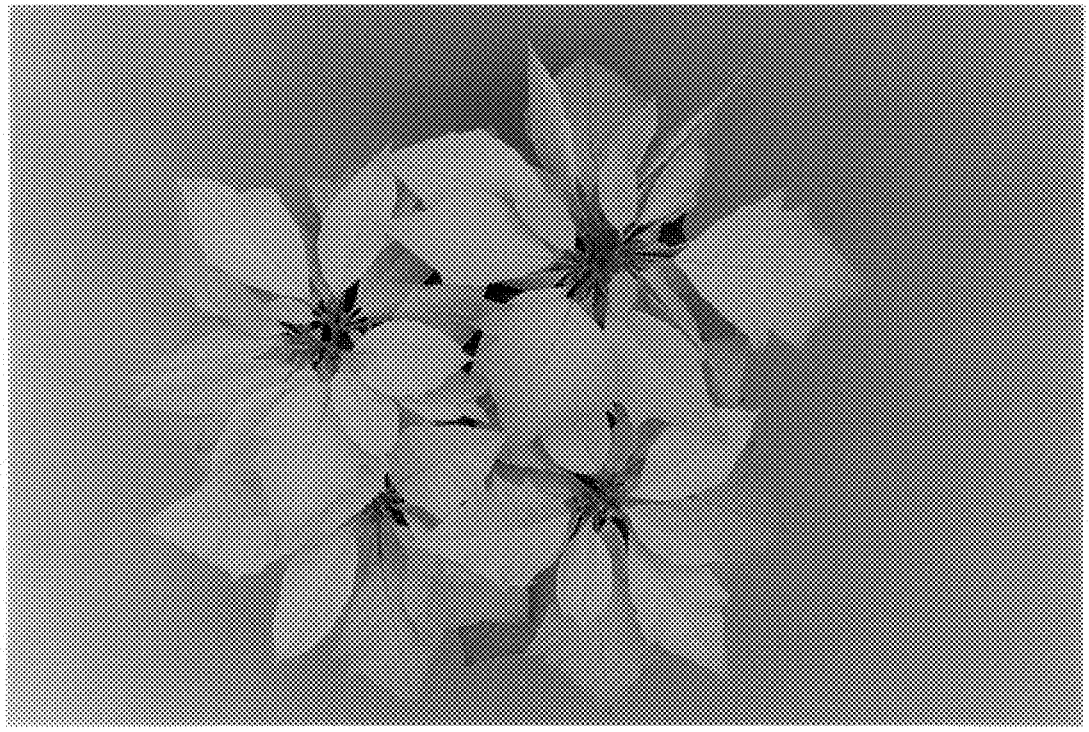
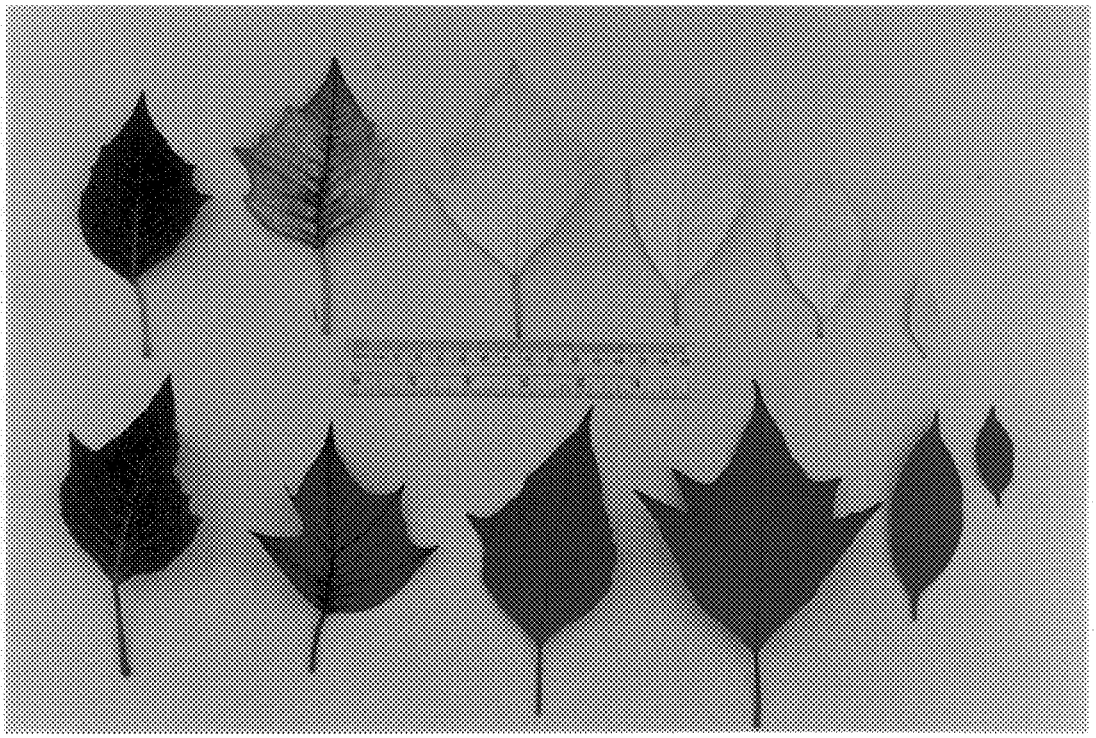

* * * * *